US007667025B2

(12) United States Patent
Smith et al.

(10) Patent No.: US 7,667,025 B2
(45) Date of Patent: Feb. 23, 2010

(54) ARTICLES OF MANUFACTURE FOR DETECTION OF HERPES SIMPLEX VIRUS

(75) Inventors: Thomas F. Smith, Rochester, MN (US); Arlo Wold, Charles, MN (US); Jim Uhl, Rochester, MN (US); Mark J. Espy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 68 days.

(21) Appl. No.: 11/140,640

(22) Filed: May 27, 2005

(65) Prior Publication Data

US 2006/0019242 A1 Jan. 26, 2006

Related U.S. Application Data

(62) Division of application No. 10/066,432, filed on Jan. 31, 2002, now Pat. No. 6,958,210.

(60) Provisional application No. 60/265,376, filed on Jan. 31, 2001.

(51) Int. Cl.
C07H 21/04 (2006.01)
(52) U.S. Cl. .................. 536/24.3; 536/24.32; 536/24.33
(58) Field of Classification Search ...................... 435/5; 536/24.3, 24.32, 24.33
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,824,776 A | 4/1989 | Heller |
| 4,965,188 A | 10/1990 | Mullis et al. |
| 4,996,143 A | 2/1991 | Heller et al. |
| 5,035,996 A | 7/1991 | Hartley |
| 5,049,490 A | 9/1991 | Sutherland et al. |
| 5,246,924 A | 9/1993 | Fox et al. |
| 5,354,653 A | 10/1994 | Matsumoto et al. |
| 5,538,848 A | 7/1996 | Livak et al. |
| 5,541,308 A | 7/1996 | Hogan et al. |
| 5,565,322 A | 10/1996 | Heller |
| 5,654,416 A | 8/1997 | Cummins et al. |
| 5,683,896 A | 11/1997 | Hartley et al. |
| 5,702,895 A | 12/1997 | Matsunaga et al. |
| 5,702,901 A | 12/1997 | Cummins et al. |
| 5,733,751 A | 3/1998 | Cummins et al. |
| 5,837,452 A | 11/1998 | Clark et al. |
| 5,846,706 A | 12/1998 | Greenberg et al. |
| 5,849,489 A | 12/1998 | Heller |
| 5,925,517 A | 7/1999 | Tyagi et al. |
| 5,945,313 A | 8/1999 | Hartley et al. |
| 6,030,115 A | 2/2000 | Ishiguro et al. |
| 6,140,054 A | 10/2000 | Wittwer et al. |
| 6,162,603 A | 12/2000 | Heller |
| 6,174,670 B1 | 1/2001 | Wittwer et al. |
| 6,245,514 B1 | 6/2001 | Wittwer |
| 6,593,093 B1 | 7/2003 | Uhl et al. |

FOREIGN PATENT DOCUMENTS

| EP | 0 269 764 | 6/1988 |
| EP | 0 338 591 | 11/1989 |
| EP | 0 526 876 | 2/1993 |
| EP | 1 045 033 | 10/2000 |
| EP | 1 160 333 | 12/2001 |
| GB | 2 252 323 | 8/1992 |
| WO | WO 90/01547 | 2/1990 |
| WO | WO 90/02802 | 3/1990 |
| WO | WO 97/46707 | 12/1997 |
| WO | WO 97/46712 | 12/1997 |
| WO | WO 97/46714 | 12/1997 |
| WO | WO 98/48046 | 10/1998 |
| WO | WO 99/19466 | 4/1999 |
| WO | WO 99/45155 | 9/1999 |
| WO | WO 00/70096 | 11/2000 |
| WO | WO 01/12803 | 2/2001 |
| WO | WO 01/23604 | 4/2001 |
| WO | WO 02/18660 | 3/2002 |
| WO | WO 02/34771 | 5/2002 |
| WO | WO 02/061390 | 8/2002 |
| WO | WO 03/068918 | 8/2003 |

OTHER PUBLICATIONS

Buck et al., BioTechniques 27, 528-536 (1999).*
GenBank Accession No. M16321 dated Aug. 2, 1993.
GenBank Accession No. M16721 dated Aug. 2, 1993.
GenBank Accession No. X01712 dated Apr. 18, 2005.
GenBank Accession No. X04771 dated Sep. 12, 1993.
GenBank Accession No. AF303108 dated Dec. 18, 2000.
GenBank Accession No. NC_001798 dated Apr. 21, 2005.
GenBank Accession No. NC_001806 dated Oct. 8, 2005.
Al-Robaiy et al., "Rapid Competitive PCR Using Melting Curve Analysis for DNA Quantification," *BioTechniques*, 2001, 31:1382-1388.
Arthur et al., "*Enterococcus faecium* transposon Tn1546 transposase, resolvase, vanR, vanS, vanH, vanA, vanX, vanY and teicoplanin resistance protein (vanZ) genes, complete CDs," 1993, database accession No. M97297.
Bassler et al., "Use of a Fluorogenic Probe in a PCR-Based Assay for the Detection of *Listeria monocytogenes*," *Appl. Environ. Microbiol.*, 1995, 61(10):3724-3728.
Bélanger et al., "Rapid Detection of Shiga Toxin-Producing Bacteria in Feces by Multiplex PCT with Molecular Beacons on the Smart Cycler," *J. Clin. Microbiol.*, 2002, 40:1436-1440.

(Continued)

Primary Examiner—Kenneth R. Horlick
(74) Attorney, Agent, or Firm—Fish & Richardson P.C.

(57) ABSTRACT

The invention provides methods to detect herpes simplex virus (HSV) in biological samples and further to distinguish between HSV-1 and HSV-2. Primers and probes for the differential detection of HSV-1 and HSV-2 are provided by the invention. Articles of manufacture containing such primers and probes for detecting HSV are further provided by the invention.

5 Claims, No Drawings

OTHER PUBLICATIONS

Bellin et al., "Rapid Detection of Enterohemorrhagic *Escherichia coli* by Real-Time PCR with Fluorescent Hybridization Probes," *J. Clin. Microbiol.*, 2001, 39:370-374.

Brink et al., "Nucleic Acid Sequence-Based Amplification, A New Method for Analysis of Spliced and Unspliced Epstein-Barr Virus Latent Transcripts, and Its Comparison with Reverse Transcriptase PCR," *J. Clin. Microbiol.*, 1998, 36(11):3164-3169.

Caplin et al., "LightCycler™ hybridization probes; The most direct way to monitor PCRamplification for quantiflcation and mutation detection," *Biochemica*, 1999, 1:5-8.

Chn et al., "An Automated Fluorescent PCR Method for Detection of Shiga Toxin-Producing *Escherichia coli* in Foods," *Appl. Environ. Microbiol.*, 1998, 64:4210.4216.

Chesky et al., "Polymerase Chain Reaction for the Laboratory Diagnosis of Aseptic Meningitis and Encephalitis," *Arq. Neuronsiquiatr.*, 2000, 58(3-B):836-842.

Didenko, "DNA Probes Using Fluorescence Resonance Energy Transfer (FRET): Designs and Applications," *BioTechniques*, 2001, 31:1106-1121.

Espy et al., "Diagnosis of Herpes Simplex Virus Infections in the Clinical Laboratory by LightCycler PCR," *J. Clin. Microbiol.*, 2000, 38(2):795-799.

Espy et al., "Evaluation of LIghtCycler PCR for Implementation of Laboratory Diagnosis of Herpes Simplex Virus Infections," *J. Clin. Microbiol.*, 2000, 38(8):3116-3118.

Espy et al., "Quantification of Epstein-Barr Virus (EBV) Viral Load in Transplant Patients by LightCycler PCR," *Abstracts of the General Meeting of the American Society for Microbiology*, 101$^{st}$ General Meeting, May 20-24, 2001, 101:182, Abstract No. C-148.

Espy et al., "Diagnosis of Varicella-Zoster Virus Infections in the Clinical Laboratory by LightCycler PCR," *J. Clin. Microbiol.*, 2000, 38(9):3187-3189.

Espy et al., "Detection of Smallpox Virus DNA by LightCycler PCR," *J. Clin. Microbiol.*, 2002, 40(6):1985-1988.

Grisold et al., "Detection of Methicillin-Resistant *Staphylococcus aureus* and Simultaneous Confirmation by Automated Nucleic Acid Extraction and Real-Time PCR," *J. Clin. Microbiol.*, 2002, 40:2392-2397.

Higuchi et al., *Bio/Technology*, 1992, 40:413-417.

Holland et al., "PCR Detection of *Escherichia coli* O157:H7 Directly from Stools: Evaluation of Commercial Extraction Methods for Purifying Fecal DNA," *J. Clin. Microbiol.*, 2000, 38:4108-4113.

Hulctsky et al., "Rapid Detection of Vancomycin-Resistant Enterococci Directly from Rectal Swabs by Real-Time PCR Using the Smart Cycler," *Abstracts of the Interscience Conference on Antimicrobial Agents and Chemotherapy*, Chicago, Illinois, Sep. 22-25, 2001, 41:409 (Abstract K-1195).

Ito et al., "*Staphylococcus aureus* DNA, type-I staphylococcal cassette chromosome mec," 1999, database accession No. AB033763.

Johnson et al., "Comprehensive PCR-Based Assay for Detection and Species Identification of Human Herpesviruses," *J. Clin. Microbiol.*, 2000, 38(9):3274-3279.

"LightCycler-FastStart DNA Master Hybridization Probes," 1999 Roche Diagnostics GmbH Technical Manual, retrieved from the internet on Feb. 6, 2004: http://www.roche-applied-science.com.

Livak et al., "Oligonucleotides with Fluorescent Dyes at Opposite Ends Provide a Quenched Probe System Useful for Detecting PCR Product and Nucleic Acid Hybridization," *Genome Research*, 1995, 4:357-362.

Livak et al., *PCR Methods and Applications*, 1995, pp. 357-362.

Machiels et al., "New Protocol for DNA Extraction of Stool," *BioTechniques*, 2000, 28:286-290.

McOrist et al., "A comparison of five methods for extraction of bacterial DNA from human faecal samples," *J. Microbiological Methods*, 2002, 50:131-139.

Palladino et al., "Real-time PCR for the rapid detection of *vanA* and *vanB* genes," *Diagnostic Microbiology and Infectious Disease*, 2003, 45:81-84.

Palladino et al., "Rapid Detection of *vanA* and *vanB* Genes Directly from Clinical Specimens and Enrichment Broths by Real-Time Multiplex PCR Assay," *J. Clin. Microbiol.*, 2003, 41:2483-2486.

Patel et al., "*Enterococcus faecalis* vancomycin resistance protein (vanB) gene, partial cds," 1997, database accession No. U72704.

Patel et al., "*Enterococcus faecium* vancomycin resistance protein B (vanB) gene, partial cds," 1997, database U94528.

Petrich et al., "Direct detection of *vanA* and *vanB* genes in clinical specimens for rapid identification of vancomycin resistant enterococci (VRE) using multiplex PCR," *Mol. Cell. Probes*, 1999, 13:275-281.

Piiparinen et al., *Arch. Virol.*, 1991, 119:275-283.

Quereda et al., "Diagnostic Utility of a Multiplex Herpesvirus PCR Assay Performed with Cerebrospinal Fluid from Human Immunodeficiency Virus-Infected Patients with Neurological Disorders," *J. Clin. Microbiol.*, 2000, 38(8):3061-3067.

Nogueira et al., "Comparison of Virus Isolation and Various Polymerase Chain Reaction Methods in the Diagnosis of Mucocutaneous Herpesvirus Infection," *Acta Virologica*, 2000, 44:61-65.

www.phenix1.com/RotorGene.asp—Rotor-Gene, Phenix Research Products, Copyright 2000.

Ramotar et al., "Direct Detection of Verotoxin-Producing *Escherichia coli* in Stool Samples by PCR," *J. Clin. Microbiol.*, 1995, 33:519-524.

Reischl et al., "Rapid Identification of Methicillin-Resistant *Staphylococcus aureus* and Simultaneous Species Confirmation Using Real-Time Fluorescence PCR," *J. Clin. Microbiol.*, 2000, 38:2429-2433.

Ryncarz et al., "Development of a High-Throughput Quantitative Assay for Detecting Herpes Simplex Virus DNA in Clinical Samples," *J. Clin. Microbiol.*, 1999, 37:1941-1947.

Sample et al., "Two Related Epstein-Barr Virus Membrane Proteins are Encoded by Separate Genes," *J. Virol.*, 1989, 63(2):933-937.

Sloan et al., "Evaluation of a Combined LightCycler Assay for the Detection of vanA, vanB, and vanB-2/3 Genes in Enterococci," *Abstracts of the General Meeting of the American Society for Microbiology*, 2002, 102:143 (Abstract C-242).

Smith, "Application of LightCycler Real Time PCR in Clinical Virology," *Clin. Chem. Lab. Med.*, 2001, Special Supplement, 39:S60, Abstract No. ISW14-2.

Studahl et al. "Herpesivrus DNA Detection in Cerebral Spinal Fluid: Differences in Clinical Presentation between Alpha-, Beta-, and Gamma-Herpesviruses," *Scand. J. Infect. Dis.*, 2000, 32:237-248.

Tang et al., "Molecular Diagnosis of Herpes Simplex Virus Infections in the Central Nervous System," *J. Clin. Microbiol*, 1999, 37(7):2127-2136.

Telenti et al., "Detection of Epstein-Barr Virus by Polymerase Chain Reaction," *J. Clin. Microbiol.*, 1990, 28(10):2187-2190.

Van der Hoek et al., "Isolation of Human Immunodeficiency Virus Type 1 (HIV-1) RNA from Feces by a Simple Method and Difference between HIV-1 Subpopulations in Feces and Serum," *J. Clin. Microbiol.*, 1995, 33:581-588.

Abd-Elsalam, Kamel, "Bioinformatic Tools and Guideline for PCR Primer Design," *African Journal of Biotechnology*, 2003, vol. 2(5): 91-95.

Ballard et al., "Comparison of Three PCR Primer Sets for Identification of *vanB* Gene Carriage in Feces and Correlation with Carriage of Vancomycin-Resistant Enterococci: Interference by *vanB*-Containing Anaerobic Bacilli," *Antimicrobial Agents and Chemotherapy*, 2005, vol. 49(1): 77-81.

Csordas et al., "Comparison of Primers for the Detection of *Salmonella enterica* Serovars Using Real-Time PCR," *Letters in Applied Microbiology*, 2004, 39: 187-193.

Elnifro et al., "Multiplex PCR: Optimization and Application in Diagnostic Virology," *Clinical Microbiology Reviews*, 2000, vol. 13(4): 559-570.

Tichopad et al., "Inhibition of Real-Time RT-PCR Quantification Due to Tissue-Specific Contaminants," *Molecular and Cellular Probes*, 2004, 18: 45-50.

GenBank Accession No. NC_004368 dated Nov. 15, 2002.

Ahern, "Biochemical, Reagent Kits Offer Scientists Good Return On Investment," *The Scientist*, 1995, 9:20.

Beards et al., "Investigation of Vesicular Rashes for HSV and VZV by PCR," *J. Med. Virol.*, 1998, 54:155-157.

Bergeron et al., "Rapid Detection of Group B Streptococci in Pregnant Women At Delivery," *N. Engl. J. Med.*, 2000, 343:175-179.

Burrows et al., "Detection and subtyping of Herpes simplex virus in clinical samples by LightCycler PCR, enzyme immunoassay and cell culture," *BMC Microbiology*, 2002, 2:12.

Davison and Scott, "The Complete DNA Sequence of Varicella-Zoster Virus," *J. Gen. Virol.*, 1986, 67:1759-1816.

Kinoshita et al., "Variation of R1Repeated Sequence Present in Open Reading Frame 11 of Varicella-Zoster Virus Strains," *J. Virol.*, 1988, 62(3):1097-1100.

Tettelin et al., "Complete genome sequence and comparative genomic analysis of an emerging human pathogen, serotype V *Streptococcus agalactiae*," *Proc. Natl. Acad. Sci. USA*, 2002, 99(19):12391-12396.

Berry et al., "Comparison of Six Real-Time PCR Assays for the Detection of Herpes Simplex Virus in Clinical Specimens," *J. Mol. Diag.*, 2006, 8(5), ID24.

* cited by examiner

ARTICLES OF MANUFACTURE FOR DETECTION OF HERPES SIMPLEX VIRUS

CROSS REFERENCE TO RELATED APPLICATIONS

This application is Divisional of and claims priority under 35 U.S.C. §120to U.S. application Ser. No. 10/066,432 having a filing date of Jan. 31, 2002, now U.S. Pat. No. 6,958,210 issued on Oct. 25, 2005, which claims the benefit of priority under 35 U.S.C. §119(e) of U.S. application No. 60/265,376, filed Jan. 31, 2001. The disclosures of prior applications are incorporated by reference in their entirety.

TECHNICAL FIELD

This invention relates to viral diagnostics, and more particularly to detection of herpes simplex virus (HSV).

BACKGROUND

Herpes simplex virus (HSV) is the virus most commonly detected in diagnostic laboratories, accounting for over 40% of the viruses that were detected in cell cultures over a 25-year period. HSV causes a variety of clinical syndromes, and anatomical sites infected include the skin, lips, oral cavity, eyes, genital tract, and central nervous system. Generalized or disseminated HSV infection may occur in patients immunologically compromised by neoplasia, organ transplantation, inherited immunodeficiency disease, or AIDS, or through neonatal infection acquired by transmission of the virus through an infected birth canal. Most disseminated disease is fatal.

SUMMARY

The invention provides for methods of identifying HSV in a biological sample, and further, for distinguishing between HSV-1 and HSV-2. Primers and probes for detecting HSV and for distinguishing between HSV-1 and HSV-2 are provided by the invention, as are kits containing such primers and probes. Methods of the invention can be used to rapidly identify HSV DNA from specimens for differential diagnosis of HSV infection. Using specific primers and probes, the method includes amplifying and monitoring the development of specific amplification products using fluorescence resonance emission technology (FRET).

In one aspect, the invention features a method for detecting the presence or absence of herpes simplex virus (HSV) in a biological sample from an individual. The method to detect HSV includes performing at least one cycling step, which includes an amplifying step and a hybridizing step. The amplifying step includes contacting the sample with a pair of HSV DNA polymerase primers to produce an HSV DNA polymerase amplification product if an HSV DNA polymerase nucleic acid molecule is present in the sample. The hybridizing step includes contacting the sample with a pair of HSV DNA polymerase probes. Generally, the members of the pair of HSV DNA polymerase probes hybridize within no more than five nucleotides of each other. A first HSV DNA polymerase probe of the pair of HSV DNA polymerase probes is typically labeled with a donor fluorescent moiety and a second HSV DNA polymerase probe of the pair of HSV DNA polymerase probes is labeled with a corresponding acceptor fluorescent moiety. The method further includes detecting the presence or absence of fluorescence resonance energy transfer (FRET) between the donor fluorescent moiety of the first HSV DNA polymerase probe and the corresponding acceptor fluorescent moiety of the second HSV DNA polymerase probe. The presence of FRET is usually indicative of the presence of HSV in the biological sample, while the absence of FRET is usually indicative of the absence of HSV in the biological sample.

Alternatively, or additionally, the amplification step can include contacting the sample with a pair of HSV TK primers to produce an HSV TK amplification product if an HSV TK nucleic acid molecule is present in the sample. The hybridizing step includes contacting the sample with a pair of HSV TK probes. Generally, the members of the pair of HSV TK probes hybridize within no more than five nucleotides of each other. A first HSV TK probe of the pair of HSV TK probes is typically labeled with a donor fluorescent moiety and a second HSV TK probe of the pair of HSV TK probes is typically labeled with a corresponding acceptor fluorescent moiety. The method further includes detecting the presence or absence of FRET between the donor fluorescent moiety of the first HSV TK probe and the acceptor fluorescent moiety of the second HSV TK probe. The presence of FRET is usually indicative of the presence of HSV in the sample, while the absence of FRET is usually indicative of the absence of HSV in the sample.

In another aspect, the invention features a method of distinguishing between HSV-1 and HSV-2 in a biological sample from an individual. The method to distinguish between HSV-1 and HSV-2 includes performing at least one cycling step of amplifying and hybridizing. The amplifying step includes contacting the sample with a pair of HSV DNA polymerase primers to produce an HSV-1 DNA polymerase amplification product if an HSV-1 DNA polymerase nucleic acid molecule is present in the sample and/or an HSV-2 DNA polymerase amplification product if an HSV-2 DNA polymerase nucleic acid molecule is present in the sample. The hybridizing step includes contacting the sample with a pair of HSV DNA polymerase probes. The members of the pair of HSV DNA polymerase primers can hybridize to sequences within an nucleic acid molecule encoding HSV DNA polymerase that are identical between HSV-1 DNA polymerase nucleic acid and HSV-2 DNA polymerase nucleic acid, while the HSV DNA polymerase probes hybridize to a sequence that differs between HSV-1 DNA polymerase nucleic acid and HSV-2 DNA polymerase nucleic acid by at least one nucleotide. Generally, a first HSV DNA polymerase probe of the pair of HSV DNA polymerase probes is labeled with a donor fluorescent moiety, and a second HSV DNA polymerase probe of the pair of HSV DNA polymerase probes is labeled with a corresponding acceptor fluorescent moiety. The method further includes detecting the presence or absence of FRET between the donor fluorescent moiety of the first HSV DNA polymerase probe and the corresponding acceptor fluorescent moiety of the second HSV DNA polymerase probe. The presence of FRET usually indicates the presence of HSV in the biological sample, and the absence of FRET usually indicates the absence of HSV in the biological sample. The melting temperature then can be determined between the HSV DNA polymerase probes and the respective amplification products to distinguish between HSV-1 and HSV-2.

A pair of HSV DNA polymerase primers generally includes a first HSV DNA polymerase primer and a second HSV DNA polymerase primer. The first HSV DNA polymerase primer can include the sequence 5'-GCT CGA GTG CGA AAA AAC GTT C-3' (SEQ ID NO:1), and the second HSV DNA polymerase primer can include the sequence 5'-CGG GGC GCT CGG CTA AC-3' (SEQ ID NO:2). The first HSV DNA polymerase probe can include the sequence 5'-GCG CAC CAG ATC CAC GCC CTT GAT GAG C-3' (SEQ ID NO:3), and the second HSV DNA polymerase probe can include the sequence 5'-CTT GCC CCC GCA GAT GAC GCC-3' (SEQ ID NO:4). Alternatively, the first HSV DNA polymerase probe can include the sequence 5'-GTA CAT CGG CGT CAT CTG CGG GGG CAA G-3' (SEQ ID NO:5), and the second HSV DNA polymerase probe can include the sequence 5'-T GCT CAT CAA GGG CGT GGA TCT GGT GC-3' (SEQ ID NO:6).

A pair of HSV TK primers generally includes a first HSV TK primer and a second HSV TK primer. The first HSV TK primer can include the sequence 5'-CAC GCT RCT GCG GGT TTA TAT AGA-3' (SEQ ID NO:7), wherein R is A or G, and the second HSV TK primer can include the sequence 5'-TTG TTA TCT GGG CGC TMG TCA TT-3' (SEQ ID NO:8), wherein M is A or C. The first HSV TK probe can include the sequence 5'-CGC GCG ACG ATA TCG TCT ACG TAC-3' (SEQ ID NO:9), and the second HSV TK probe can include the sequence 5'-CGA GCC GAT GAC TTA CTG GCA GGT G-3' (SEQ ID NO:10).

The members of a pair of HSV DNA polymerase probes can hybridize within no more than two nucleotides of each other, or can hybridize within no more than one nucleotide of each other. A representative donor fluorescent moiety is fluorescein, and corresponding acceptor fluorescent moieties include LC-Red 640, LC-Red 705, Cy5, and Cy5.5. Additional corresponding donor and acceptor fluorescent moieties are known in the art.

In one aspect, the detecting step includes exciting the biological sample at a wavelength absorbed by the donor fluorescent moiety and visualizing and/or measuring the wavelength emitted by the corresponding acceptor fluorescent moiety. In another aspect, the detecting step includes quantitating the FRET. In yet another aspect, the detecting step can be performed after each cycling step (e.g., in real-time).

Generally, the presence of the FRET within 50 cycles (e.g., 10, 20, 30, 37, 40 or 45 cycles) indicates the presence of an HSV infection in the individual. Typically, the presence of FRET within 37 cycles indicates the presence of an HSV infection in the individual, while the absence of FRET within 37 cycles indicates the absence of an HSV infection in the individual.

Representative biological samples that can be used in the methods of the invention include an ocular swab, a genital specimen, a dermal specimen, a pap smear, amniotic fluid and cerebrospinal fluid. The above-described methods can further include preventing amplification of a contaminant nucleic acid. Preventing amplification can include performing the amplifying steps in the presence of uracil and treating the biological samples with uracil-DNA glycosylase prior to amplifying. In addition, the cycling step can be performed on a control sample. A control sample can include the same portion of the HSV DNA polymerase or HSV TK nucleic acid molecule. Alternatively, a control sample can include a nucleic acid molecule other than an HSV DNA polymerase or HSV TK nucleic acid molecule. Cycling steps can be performed on such a control sample using a pair of control primers and a pair of control probes. The control primers and probes are other than HSV DNA polymerase or HSV TK primers or probes. Each of the control probes hybridizes to the control amplification product.

In another aspect of the invention, there are provided articles of manufacture, or kits. Kits of the invention can include a pair of HSV DNA polymerase primers, a pair of HSV DNA polymerase probes, and a donor and corresponding acceptor fluorescent moiety. For example, a first HSV DNA polymerase primer provided in a kit of the invention can include the sequence 5'-GCT CGA GTG CGA AAA AAC GTT C-3' (SEQ ID NO:1), and a second HSV DNA polymerase primer can include the sequence 5'-CGG GGC GCT CGG CTA AC-3' (SEQ ID NO:2). A first HSV DNA polymerase probe provided in a kit of the invention can include the sequence 5'-GCG CAC CAG ATC CAC GCC CTT GAT GAG C-3' (SEQ ID NO:3), and the second HSV DNA polymerase probe can include the sequence 5'-CTT GCC CCC GCA GAT GAC GCC-3' (SEQ ID NO:4). Alternatively, the first HSV DNA polymerase probe provided in a kit of the invention can include the sequence 5'-GTA CAT CGG CGT CAT CTG CGG GGG CAA G-3' (SEQ ID NO:5), and the second HSV DNA polymerase probe can include the sequence 5'-T GCT CAT CAA GGG CGT GGA TCT GGT GC-3' (SEQ ID NO:6).

Articles of manufacture or kits of the invention can further include a pair of HSV TK primers, a pair of HSV TK probes, and a donor and corresponding acceptor fluorescent moiety. For example, a first HSV TK primer provided in a kit of the invention can include the sequence 5'-CAC GCT RCT GCG GGT TTA TAT AGA-3' (SEQ ID NO:7), wherein R is A or G, and a second HSV TK primer can include the sequence 5'-TTG TTA TCT GGG CGC TMG TCA TT-3' (SEQ ID NO:8), wherein M is A or C. A first HSV TK probe provided in a kit of the invention can include the sequence 5'-CGC GCG ACG ATA TCG TCT ACG TAC-3' (SEQ ID NO:9), and a second HSV TK probe can include the sequence 5'-CGA GCC GAT GAC TTA CTG GCA GGT G-3' (SEQ ID NO:10). Articles of manufacture can include fluorophoric moieties for labeling the probes or the probes can already be labeled with donor and corresponding acceptor fluorescent moieties. The article of manufacture also can include a package insert having instructions thereon for using the primers, probes, and fluorophoric moieties to detect the presence or absence of HSV in a biological sample and can further include instructions thereon for using the probes to distinguish between HSV-1 and HSV-2.

In yet another aspect of the invention, there is provided a method for detecting the presence or absence of HSV in a biological sample from an individual. Such a method includes performing at least one cycling step. A cycling step can include an amplifying step and a hybridizing step. Generally, an amplifying step includes contacting the sample with a pair of HSV DNA polymerase primers to produce an HSV DNA polymerase amplification product if a nucleic acid molecule encoding HSV DNA polymerase is present in the sample. Generally, a hybridizing step includes contacting the sample with an HSV DNA polymerase probe. Such an HSV DNA polymerase probe is usually labeled with a donor fluorescent moiety and a corresponding acceptor fluorescent moiety. The method further includes detecting the presence or absence of fluorescence resonance energy transfer (FRET) between the donor fluorescent moiety and the corresponding acceptor fluorescent moiety of the HSV DNA polymerase probe. The presence or absence of FRET is indicative of the presence or absence of HSV in said sample. In addition to the HSV DNA polymerase primers and probe described herein, this method also can be performed using HSV TK primers and probe.

In one aspect, amplification can employ a polymerase enzyme having 5' to 3' exonuclease activity. Thus, the donor and acceptor fluorescent moieties are within no more than 5 nucleotides of each other along the length of the probe. In another aspect, the HSV DNA polymerase probe includes a nucleic acid sequence that permits secondary structure formation. Such secondary structure formation generally results in spatial proximity between the donor and acceptor fluorescent moiety. According to this method, the acceptor fluorescent moiety on a probe can be a quencher.

In another aspect of the invention, there is provided a method for detecting the presence or absence of HSV in a biological sample from an individual. Such a method includes performing at least one cycling step. A cycling step can include an amplifying step and a dye-binding step. An amplifying step generally includes contacting the sample with a pair of HSV DNA polymerase primers to produce an HSV DNA polymerase amplification product if a nucleic acid molecule encoding HSV DNA polymerase is present in the sample. A dye-binding step generally includes contacting the HSV DNA polymerase amplification product with a nucleic acid binding dye. The method further includes detecting the presence or absence of binding of the nucleic acid binding dye to the amplification product. According to the invention, the presence of binding is typically indicative of the presence of HSV in the sample, and the absence of binding is typically indicative of the absence of HSV in the sample. Such a method can further include the steps of determining the melting temperature between the HSV DNA polymerase amplification product and the nucleic acid binding dye. Generally, the melting temperature confirms the presence or absence of HSV. Representative nucleic acid binding dyes include SYBRGreenI®, SYBRGold®, and ethidium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

The present invention provides for methods of detecting HSV in a biological sample, and further for distinguishing between HSV-1 and HSV-2 infections. Primers and probes for detecting HSV-1 and HSV-2 are provided, as are articles of manufacture containing such primers and probes. The detection of HSV from genital, dermal, and ocular sources was compared herein using LightCycler™ PCR (Roche Molecular Biochemicals; Indianapolis, Ind.), shell vial and cell culture methods. The increased sensitivity of LightCycler™ PCR compared to other methods and the instrument's features for sample containment and real-time detection of the amplified product indicate the feasibility for implementation of this technology for routine diagnosis of HSV infection in the clinical laboratory.

Herpes Simplex Virus (HSV)

HSV causes, or is associated with, a wide variety of diseases in humans such as genital lesions, stomatitis, encephalitis, herpetic dermatitis, meningitis, pharyngitis, keratoconjunctivitis, pneumonia, neonatal herpes, keratitis, chorioretinitis, herpetic hepatitis, eczema herpeticum and erythema multiforme. Herpes simplex virus types 1 and 2 (HSV-1 and HSV-2) infect a large number of individual each year. HSV-1 infection typically produces skin vesicles or mucosal ulcers generally limited to the oropharynx, while HSV-2 typically produces mucocutaneous lesions generally in the genital region. HSV-2 is one of the most common sexually transmitted diseases in society. There are instances in which rapid, sensitive, and specific diagnosis of HSV disease is imperative. The most serious HSV infection is encephalitis. Encephalitis is often a disseminated infection in newborns that may be acquired either during or after birth; and an adult infection affects the temporal lobe of the brain. Currently, definitive diagnosis is by brain biopsy and culture to isolate HSV. Serologic diagnosis, particularly of HSV in cerebrospinal fluid (CSF), is not sufficiently sensitive or specific, and takes too much time to be of use in decisions involving choices for early therapeutic intervention of encephalitis. Early therapy of patients with encephalitis, before irreversible hemorrhagic necrosis of the brain, has resulted in improved outcomes. Further, due to the high morbidity and mortality of infants having neonatal herpes infection, and since many cases of neonatal HSV infection can be prevented by cesarean section, diagnosis of maternal infection before delivery is important. Since cultures of the mother taken days or weeks before delivery do not predict well whether the mother may be symptomatic at the time of delivery, a rapid, sensitive, and specific assay for detecting HSV in body fluids or secretions is desirable as a means to monitor infection, and consequently, determine the necessity of cesarean section.

Additionally, there are instances in which knowing whether the infection is cause by HSV-1 or HSV-2. Since both HSV-1 and HSV-2 share antigens, serological differentiation is difficult. Distinguishing between infection caused by HSV-1 and HSV-2 may be important because sensitivity to antiviral therapy can vary with the serotype. Identifying the serotype can also provide prognostic information. For example, genital infections caused by HSV-1 are less likely to recur than those infections caused by HSV-2.

HSV Nucleic Acids and Oligonucleotides

All herpes simplex viruses have a linear double-stranded DNA genome and all replicate in the nucleus of infected cells where viral gene expression during viral replication occurs as an ordered cascade. Genes expressed during viral replication are organized on the genome in a very specific manner; there are few overlapping genes, very few spliced genes, and regulatory elements (for example, promoters) are immediately upstream of the open reading frames. All known herpes viruses have three major classes of genes, α, β, and γ, which have the same basic temporal pattern of expression during the viral lifestyle.

Alpha genes, also called immediate-early genes, are expressed very early after infection and the expression of each alpha gene does not require any other viral gene or gene product. The products of the alpha genes are predominantly involved in regulation of viral gene expression. Beta (early) genes are expressed only after the alpha genes because their expression depends on the presence of one or more of the alpha gene products that act as transcriptional activators to up-regulate the expression of the beta genes. The products of beta genes are primarily enzymes involved in viral nucleic acid synthesis and metabolism. Sequence analysis data has shown that the beta genes represent a limited number of genes in the genomes of all herpes simplex viruses that have been studied and that beta genes are highly conserved within the herpesvirus family. Gamma (late) genes are expressed either primarily (γ1) or exclusively (γ2) following viral DNA synthesis. Gamma gene products are typically structural components of the virion.

The complete genomes of human HSV-1 and HSV-2 have been sequenced (see, for example, GenBank Accession Nos. NC 001806 and NC 001798, respectively). Many of the important and essential HSV genes have been identified, and can be used in polymerase chain reaction (PCR) methods such as those described by the present invention to detect HSV. For example, in HSV-1 there are fourteen genes that have been classified as beta genes: UL2, UL5, UL8, UL9, UL12, UL23, UL29, UL30, UL39, UL40, UL42, UL50, UL52, and UL53 (Roizman et al., *Herpes Simplex Viruses and Their Replication*, Raven Press, Ltd. NY, pp 1795-1841, 1990). These genes encode respectively, a uracil DNA glycosidase, a DNA helicase, a component of the DNA helicase/primase complex, an origin of DNA replication binding protein, a DNA exonuclease, a nucleoside kinase, a single-stranded DNA binding protein, a DNA polymerase, a ribonucleotide reductase large subunit, a ribonucleotide reductase small subunit, a double-stranded DNA binding protein which acts as a polymerase processivity factor, a dUTPase, a primase, and a protein kinase. All but one of these enzymes, the protein kinase, has been shown to be involved in DNA metabolism or to be directly involved in synthesis of viral DNA.

Based on standard DNA and predicted protein sequence alignment paradigms, it has been determined that HSV-2 has homologs for each of the fourteen HSV-1 beta genes (Davison et al., *J. Gen. Virol.* 67:1759-1816 1986). For example, the UL39 gene of HSV-1 encodes the large subunit of ribonucleotide reductase (RR), a two-subunit enzyme involved in the generation of deoxyribonucleoside triphosphates. The ribonucleotide reductase large subunit of HSV-1, also known as RR1 or ICP6, has 38% homology at the N-terminal portion and 93% homology at the C-terminal portion of the corresponding HSV-2 protein, ICP10, which is encoded by the UL39 gene of HSV-2. (Nikas et al. *PROTEINS. Structure, Function, and Genetics* 1:376-384, 1986).

Methods of the invention can be used to detect HSV and to differentiate between HSV-1 and HSV-2 by amplifying nucleic acid molecules encoding, for example, HSV DNA polymerase and/or HSV thymidine kinase (TK). HSV nucleic acid molecules other than those exemplified herein (e.g., other than those encoding HSV DNA polymerase or TK) also can be used to detect HSV in a sample and are known to those of skill in the art. Nucleic acid sequences encoding HSV-1 and HSV-2 DNA polymerase are available (see, for example, GenBank Accession Nos. X04771 and M16321, respectively), as are nucleic acid sequences encoding HSV-1 and HSV-2 TK (see, for example, GenBank Accession Nos. AF 303108 and X01712, respectively). Nucleic acid molecules encoding HSV-1 and HSV-2 DNA polymerase exhibit about 73% sequence identity, while nucleic acid molecules encoding HSV-1 and HSV-2 TK exhibit about 77% sequence identity. Specifically, primers and probes to amplify and detect HSV DNA polymerase nucleic acid molecules are provided by the invention, as are primers and probes to amplify and detect HSV TK nucleic acid molecules.

Primers that amplify HSV nucleic acid molecules, e.g., HSV DNA polymerase or TK, can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). To design primers that amplify nucleic acid molecules encoding DNA polymerase or TK from both HSV-1 and HSV-2, primer targets are selected within the nucleic acid molecule encoding HSV DNA polymerase or HSV TK that are identical in sequence between HSV-1 and HSV-2. Typically, oligonucleotide primers are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "HSV DNA polymerase primers" and "HSV TK primers" as used herein refers to oligonucleotide primers that specifically anneal to nucleic acid sequences encoding HSV DNA polymerase and HSV TK, respectively, and initiate synthesis therefrom under appropriate conditions.

Designing oligonucleotides to be used as hybridization probes can be performed in a manner similar to the design of primers, although the members of a pair of probes preferably anneal to an amplification product within no more than 5 nucleotides of each other on the same strand such that FRET can occur (e.g., within no more than 1, 2, 3, or 4 nucleotides of each other). This minimal degree of separation typically brings the respective fluorescent moieties into sufficient proximity such that FRET can occur. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a mutation or polymorphism, thereby allowing differential detection of HSV (e.g., HSV-1 vs. HSV-2) based on either absolute hybridization of different pairs of probes corresponding to the species to be distinguished or differential melting temperatures between, for example, members of a pair of probes and each amplification product corresponding to the species to be distinguished (e.g., HSV-1 and HSV-2). As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "HSV DNA polymerase probes" and "HSV TK probes" as used herein refers to oligonucleotide probes that specifically anneal to HSV DNA polymerase and HSV TK amplification products, respectively.

Constructs of the invention include vectors containing an HSV nucleic acid molecule, e.g., DNA polymerase or TK, or a fragment thereof. Constructs of the invention can be used, for example, as control template nucleic acid molecules. Vectors suitable for use in the present invention are commercially available and/or produced by recombinant DNA technology methods routine in the art. Nucleic acid molecules encoding HSV DNA polymerase or HSV TK can be obtained, for example, by chemical synthesis, direct cloning from HSV, or by PCR amplification. An HSV DNA polymerase or HSV TK nucleic acid molecule or fragments thereof can be operably linked to a promoter or other regulatory element such as an enhancer sequence, a response element or an inducible element that modulates expression of the HSV DNA polymerase or HSV TK nucleic acid molecule. As used herein, operably linking refers to connecting a promoter and/or other regulatory elements to a nucleic acid molecule encoding an HSV DNA polymerase or HSV TK in such a way as to permit and/or expression of the HSV DNA polymerase or HSV TK nucleic acid molecule. A promoter that does not normally direct expression of HSV DNA polymerase or HSV TK can be used to direct transcription of a DNA polymerase or HSV TK nucleic acid using, for example, a viral polymerase, a bacterial polymerase, or a eukaryotic RNA polymerase. Alternatively, the HSV DNA polymerase or HSV TK native promoter can be used to direct transcription of an HSV DNA polymerase or HSV TK nucleic acid, respectively. In addition, operably linking can refer to an appropriate connection between an HSV DNA polymerase or HSV TK promoter or regulatory element and a heterologous coding sequence (e.g., a non-HSV coding sequence or a non-DNA polymerase or -TK coding sequence, for example, a reporter gene) in such a way as to permit expression of the heterologous coding sequence.

Constructs suitable for use in the methods of the invention typically include, in addition to nucleic acid molecules encoding HSV DNA polymerase or HSV TK, nucleic acid sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing nucleic acid molecules encoding HSV DNA polymerase or HSV TK can be propagated in a host cell. As used herein, the term host cell is meant to include prokaryotes and eukaryotes such as yeast, plant and animal cells. Prokaryotic hosts may include *E. coli, Salmonella tymphimurium, Serratia marcescens* and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium. phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within nucleic acid molecules encoding HSV DNA polymerase or HSV TK. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min.

If the double-stranded nucleic acid is denatured by heat, the reaction mixture is allowed to cool to a temperature that promotes annealing of each primer to its target nucleic acid sequence. The temperature for annealing is usually from about 35° C. to about 65° C. Annealing times can be from about 10 secs to about 1 min. The reaction mixture is then adjusted to a temperature at which the activity of the polymerase is promoted or optimized, i.e., a temperature sufficient for extension to occur from the annealed primer and to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° to 80° C.). Extension times can be from about 10 secs to about 5 mins.

PCR assays can employ template nucleic acid such as DNA or RNA, including messenger RNA (mRNA). The template nucleic acid need not be purified; it may be a minor fraction of a complex mixture, such as HSV nucleic acid contained in human cells. DNA or RNA may be extracted from a biological sample such as ocular swabs, genital specimens, dermal specimens, pap smears, amniotic fluid, and cerebrospinal fluid by routine techniques such as those described in *Diagnostic Molecular Microbiology: Principles and Applications* (Persing et al. (eds), 1993, American Society for Microbiology, Washington D.C). Template nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 1.5 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target HSV nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. The number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescent Resonance Energy Transfer (FRET)

FRET technology (see, for example, U.S. Pat. Nos. 4,996, 143, 5,565,322, 5,849,489, and 6,162,603) is based on the concept that when a donor and a corresponding acceptor fluorescent moiety are positioned within a certain distance of each other, energy transfer takes place between the two fluorescent moieties that can be visualized or otherwise detected and/or quantitated. Two oligonucleotides probes, each containing a fluorescent moiety, can hybridize to an amplification product at particular positions determined by the complementarity of the oligonucleotide probes to the HSV target nucleic acid sequence. Upon hybridization of the oligonucleotide probes to the amplification product at the appropriate positions, a FRET signal is generated. Hybridization temperatures can range from about 35° C. to about 65° C. for about 10 seconds to about 1 minute.

Fluorescent analysis can be carried out with a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding an acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of the linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of Herpes Simplex Virus

Cell culture is the current "gold standard" diagnostic method for detection of HSV from genital and dermal sources, producing detection rates that typically exceed 30%. HSV replicates optimally in human diploid fibroblast cell cultures. Modifications to standard cell culture techniques reduce diagnostic time to 24 to 48 h post-inoculation, but require supplemental use of conventional tube cell cultures to ultimately achieve maximum diagnostic sensitivity. Similarly, attempts at direct detection of HSV from clinical specimens by enzyme-linked immunosorbent assay (ELISA) and latex agglutination, nucleic acid probe, and fluorescent antibody methods generally fail when low titers of HSV are present in specimens used to inoculate into cell cultures.

Several recent studies have indicated the potential for increased detection of HSV infections by PCR compared to antigen detection or cell culture methods, particularly in CSF. However, routine implementation of nucleic acid amplification techniques in the clinical laboratory for dermal, genital, and other specimens has not been practical because of concerns of amplicon carryover contamination, false-positives, false-negatives, and technically cumbersome PCR product detection methods. The methods provided by the invention are highly specific and sensitive and the one-step containment provided by real-time PCR makes routine clinical diagnosis of HSV feasible.

The present invention provides for methods of detecting the presence or absence of HSV in a biological sample from an individual. This method avoids problems of sample contamination, false-negatives, false-positives and provides the further advantage of being able to distinguish HSV-1 from HSV-2. The method includes performing at least one cycling step, which first includes contacting the biological sample with a pair of HSV DNA polymerase primers to produce an HSV DNA polymerase amplification product if a nucleic acid molecule encoding HSV DNA polymerase is present in the sample. Each of the HSV DNA polymerase primers anneals to a target within or adjacent to an HSV DNA polymerase nucleic acid molecule such that at least a portion of each amplification product contains nucleic acid sequence encoding HSV DNA polymerase. More importantly, the amplification product should contain the nucleic acid sequences that are complementary to HSV DNA polymerase probes. Each cycling step further includes contacting the sample with a pair of HSV DNA polymerase probes. According to the invention, one member of the pair of HSV DNA polymerase probes is labeled with a donor fluorescent moiety and the other is labeled with a corresponding acceptor fluorescent moiety. The presence or absence of FRET between the donor fluorescent moiety of the first HSV DNA polymerase probe and the corresponding acceptor fluorescent moiety of the second HSV DNA polymerase probe is detected upon hybridization of the probes to the HSV DNA polymerase amplification product. Multiple cycles of amplification and hybridization steps can be performed, and can be performed in a thermocycler.

The above-described methods for detecting HSV in a biological sample using nucleic acid molecules encoding HSV DNA polymerase as a template also can be performed using nucleic acid molecules encoding HSV TK as a template. Such a method utilizes HSV TK primers and HSV TK probes. In most cases, the methods of the invention provide sufficient specificity that only a single target is required for diagnosis (e.g., either HSV DNA polymerase or HSV TK). If desired, detecting a second template nucleic acid can be used as a confirmatory test.

As used herein, "amplifying" refers to the process of synthesizing multiple nucleic acid molecules that are complementary to one or both strands of a template nucleic acid molecule (e.g., nucleic acid molecules encoding HSV DNA polymerase or HSV TK). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

If amplification of HSV nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of HSV in the biological sample, and the absence of FRET indicates the absence of HSV in the biological sample. Representative biological samples that can be used in practicing the methods of the invention include dermal specimens, genital specimens, ocular swabs, pap smears, amniotic fluid or cerebrospinal fluid. Biological samples are generally processed (e.g., by nucleic acid extraction methods known in the art) to release HSV nucleic acid or in some cases, the biological sample can be contacted directly with the PCR reaction components and the appropriate oligonucleotides.

A positive FRET result indicates the presence of HSV nucleic acid in the biological sample. According to the present invention, the presence of FRET within 50 cycles (for example, within 40 cycles, 37 cycles, 30 cycles, 20 cycles or 10 cycles) indicates the presence of HSV nucleic acid in the sample and usually is associated with an HSV infection in the individual examined. However, the presence of HSV nucleic acid in a biological sample may not necessarily correlate with an HSV infection in the individual. As described herein, greater than 95% of the individuals examined with LightCycler™ PCR in which FRET was detected within 37 cycles using HSV nucleic acid molecules encoding DNA polymerase were positive for an HSV infection based on a confirmatory LightCycler™ PCR assay using HSV nucleic acid molecules encoding TK. Thus, samples in which FRET was detected within 37 cycles were reported out as positive for HSV infection. The specificity of the methods was slightly reduced when FRET was detected after 37 cycles. For example, the absence of FRET prior to 38 cycles suggested that the sample should be retested or cultured using conventional methods at the primary physician's discretion. As described herein, the presence of FRET after 39 cycles was reported out as a negative HSV infection. The number of cycling steps required for accurate detection of HSV is dependent upon the cycling conditions (e.g., buffers, temperatures, and primers and probes).

A negative result indicates the absence of detectable HSV nucleic acid in the specimen submitted for analysis, but does not negate the possibility of the organism's presence in very small quantities. In the case of a negative result, it may be beneficial to study additional or alternate specimens. In the event of a negative result, the patient's primary physician should make the decision whether or not to retest the patient based on the total clinical picture. Inadequate specimen collection, transportation delays, inappropriate transportation conditions, or use of certain collection swabs (calcium alginate or aluminum shaft) are all conditions that can affect the success and/or accuracy of the test result.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the HSV DNA polymerase probes or the HSV TK probes from the respective amplification product can confirm the presence of HSV-1 and/or HSV-2 and can be used to distinguish between HSV-1 and/or HSV-2 in the sample.

Within each thermocycler run, control samples are cycled as well. Positive control samples can amplify HSV control nucleic acid template (other than the HSV DNA polymerase or HSV TK template) using, for example, control primers and control probes. Positive control samples can also amplify, for example, a plasmid construct containing HSV DNA polymerase or HSV TK nucleic acid. Such a plasmid control can be amplified internally (e.g., within each biological sample)

or in a separate sample run side-by-side with the patients' samples. Each thermocycler run should also include a negative control that, for example, lacks HSV template nucleic acid. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

Conventional PCR methods utilizing FRET technology can be used to practice the methods of the invention. In one embodiment, a LightCycler™ instrument is used. A detailed description of the LightCycler™ System and real-time and on-line monitoring of PCR can be found at http://biochem.roche.com/lightcycler. The following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LightCycler™ thermal chamber. Addition of selected fluorescent dyes to the reaction components allows the PCR to be monitored in real-time and on-line. Furthermore, the cuvettes serve as optical elements for signal collection (similar to glass fiber optics), concentrating the signal at the tip of each cuvette. The effect is efficient illumination and fluorescent monitoring of microvolume samples.

The LightCycler™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LightCycler™ apparatus, houses the light source. The emitted light is filtered and focused by an epi-illumination lens onto the top of each cuvette. Fluorescent light emitted from the sample is then focused by the same lens, passed through a dichroic mirror, filtered appropriately, and focused onto data-collecting photohybrids. The optical unit currently available in the LightCycler™ instrument (Roche Molecular Biochemicals. Catalog No. 2 011 468) includes three bandpass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LightCycler™ can be operated using a PC workstation and can utilize a Windows NT operating system. Signals from the samples are obtained as the machine positions the cuvettes sequentially over the optical unit. The software can display the fluorescence signals in real-time immediately after each measurement. Fluorescent acquisition time is 10-100 msec. After each cycling step, a quantitative display of fluorescence vs. cycle number can be continually updated for all samples. The data generated can be stored for further analysis.

A common FRET technology format utilizes two hybridization probes as described above. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler™ Instrument. During FRET, the fluorescein transfers its energy to an acceptor fluorescent moiety such as LightCycler™-Red 640 (LC™-Red 640) or LightCycler™-Red 705 (LC™-Red 705). The acceptor fluorescent moiety then emits light of a longer wavelength, which is detected by the optical detection system of the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of HSV genomes).

Another FRET technology format utilizes TaqMan® technology to detect the presence or absence of an amplification product, and hence, the presence or absence of HSV. TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TaqMan® technology, and is suitable for performing the methods described herein for detecting HSV. Information on PCR amplification and detection using an ABI PRISM® 770 system can be found at http://www.appliedbiosystems.com/products.

Yet another FRET technology format utilizes molecular beacon technology to detect the presence or absence of an amplification product, and hence, the presence or absence of HSV. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

As an alternative to detection using FRET technology, an amplification product can be detected using a nucleic acid binding dye such as a fluorescent DNA binding dye (e.g., SYBRGreenI® or SYBRGold® (Molecular Probes)). Upon interaction with the nucleic acid, such fluorescent DNA binding dyes emit a fluorescence signal after excitation with light at a suitable wavelength. A nucleic acid binding dye such as an intercalating dye also can be used. When nucleic acid binding dyes are used, a melting curve analysis is usually performed for confirmation of the presence of the amplification product.

It is understood that the present invention is not limited by the configuration of one or more commercially available instruments.

Articles of Manufacture

The invention further provides for articles of manufacture to detect HSV. An article of manufacture according to the present invention can include primers and probes used to detect HSV, together with suitable packaging material. Representative primers and probes for detection of HSV are capable of hybridizing to nucleic acid molecules encoding HSV DNA polymerase or HSV TK. Methods of designing primers and probes are disclosed herein, and representative examples of primers and probes that hybridize to nucleic acids encoding HSV DNA polymerase or HSV TK are provided.

Articles of manufacture of the invention can also include one or more fluorescent moieties for labeling the probes, or alternatively, the probes supplied with the kit can be labeled. For example, an article of manufacture may include a donor fluorescent moiety for labeling one of the HSV DNA polymerase probes or HSV TK probes and an acceptor fluorescent moiety for labeling the other HSV DNA polymerase probe or HSV TK probe, respectively. Examples of suitable FRET donor fluorescent moieties and corresponding acceptor fluorescent moieties are provided herein.

Articles of manufacture of the invention also can contain a package insert or package label having instructions thereon for using the HSV DNA polymerase primers and probes or the HSV TK primers and probes to detect HSV in a biological sample. Such a package insert may further contain instructions thereon for using HSV DNA polymerase primers and probes or HSV TK primers and probes to distinguish between HSV-1 and HSV-2 within the same biological sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

Specimens and Shell Vial Assay

Genital (n=160), dermal (n=38), and ocular (n=2) swab specimens from patients suspected of having HSV infections were extracted into 2-ml volumes of serum free medium, and the specimen extract volumes were divided into two equal aliquots. Each of two shell vial MRC-5 cell cultures received 0.2 ml of inoculum from one aliquot. The vials were centrifuged, incubated overnight at 36° C., and stained by the indirect immunofluorescence test as previously described (Gleaves et al., 1985, *J. Clin. Microbiol.*, 21:29-32).

Example 2

Nucleic Acid Extraction

Nucleic acids were extracted from a 0.2-ml volume of serum-free extract of genital, dermal, ocular swab specimens by the IsoQuick procedure (Orca Research, Inc.; Bothell, Wash.) according to manufacturer's instructions. The sample and an equal volume of lysis buffer were placed in a 1.5-ml microcentrifuge tube. A 700-µl volume of extraction matrix and a 400-µl volume of extraction buffer were added to the tube, and the tube was centrifuged for 5 min at 13,000 rpm (Eppendorf Model 5417C; Fisher; Eden Prairie, Minn.). The top aqueous layer was placed in a fresh tube and sodium acetate (1/10 volume), and 2 µl each of glycogen and isopropyl alcohol were added. The tube was then centrifuged for 10 min at 13,000 rpm (Eppendorf Model 5417C). The alcohol was poured off, and 2 volumes of 70% ethanol were added; the tube was then centrifuged for 5 min at 13,000 rpm (Eppendorf Model 5417C). The ethanol was aspirated from the tube and the pellet was resuspended in 60 µl of RNase-free water.

Example 3

LightCycler™ PCR Using HSV Nucleic Acid Encoding DNA Polymerase

Primers and probes that hybridize to HSV nucleic acid encoding DNA polymerase are shown in Table 1. One probe was labeled on the 3' end with fluorescein, while the second probe was labeled at the 5' end with LC™-Red 640. The emitted signal is proportional to the amount of specific PCR product. Ten 10-fold dilutions of a plasmid containing a portion of the HSV DNA polymerase gene were used to determine the sensitivity of the LightCycler™ assay. 20 genomic copies of HSV were detectable with the LightCycler™ assay.

TABLE 1

Primers and probes that hybridize to HSV nucleic acid encoding DNA polymerase

| Type | Product Size (bp) | Sequences (5' to 3') | SEQ ID NO: |
|---|---|---|---|
| Primer | 215 | gctcgagtgcgaaaaaacgttc | 1 |
| Primer | 215 | cggggcgctcggctaac | 2 |
| Probe (Set A) |  | gcgcaccagatccacgcccttgatgagc | 3 |
| Probe (Set A) |  | cttgccccgcagatgacgcc | 4 |
| Probe (Set B) |  | gtacatcggcgtcatctgcggggcaag | 5 |
| Probe (Set B) |  | tgctcatcaagggcgtggatctggtgc | 6 |

For the assay, a 5-µl aliquot of extracted nucleic acid was added to 15 µl of PCR mixture in each reaction capillary. A no-template control received 15 µl of reaction mixture with 5 µl of water. A master mix was optimized for the LightCycler™ and contained the following: a 0.2 mM concentration of each of the deoxyribonucleoside triphosphates (50 mM KCl, 10 mM TrisCl [pH 8.3]), 3 mM $MgCl_2$, 0.7 µM DNA polymerase primers, 0.025% bovine serum albumin, 2% dimethyl sulfoxide, 0.2 µM fluorescein-labeled DNA polymerase probe, 0.2 µM LC-Red 640-labeled DNA polymerase probe, and 0.03 U of Platinum® Taq (Perkin-Elmer Corp.; Branchburg, N.J.) per ml. The PCR reagents and specimen extracts were centrifuged in the capillary to facilitate mixing. All capillaries were then sealed and the LightCycler™ HSV-DNA polymerase program was run. Samples underwent 45 cycles of: denaturation at about 95° C. immediately followed by primer annealing to the template nucleic acid for about 10 secs at about 62° C., and elongation of the newly-synthesized strands at about 72° C. for about 12 secs. A total of 28 specimens, including the controls, were processed in a single run.

Example 4

Melting Curve for HSV Genotype Analysis

Hybridization probes were designed to be complementary to HSV-2, and sequence differences between HSV-2 and HSV-1 were detected by melting curve analysis. Melting curve analysis was performed following LightCycler™ PCR amplification. Starting at 54° C., the temperature in the thermal chamber was slowly raised to 95° C., and the fluorescence was measured at frequent intervals. Sequence differences between the DNA polymerase amplification product and probes resulted in shifts in the melting temperatures (66.7° C. for HSV-1 and 74.7° C. for HSV-2) that were detected. Analysis of the amplification product and probes melting curves was accomplished using LightCycler™ software supplied with the instrument.

Example 5

LightCycler™ PCR Using HSV Nucleic Acid Encoding Thymidine Kinase (TK)

Specimens yielding shell vial-negative, LightCycler™ PCR-positive results were resolved as true-positive samples for HSV DNA by using primers and probes that hybridize to HSV nucleic acid encoding TK.

TABLE 2

Primers and probes that hybridize to HSV nucleic acid encoding TK

| Type | Product Size (bp) | Sequences (5' to 3') | SEQ ID NO: |
|---|---|---|---|
| Primer | 335 | cacgctrctgcgggtttatataga | 7 |
| Primer | 335 | ttgttatctgggcgctmgtcatt | 8 |
| Probe |  | cgcgcgacgatatcgtctacgtac | 9 |
| Probe |  | cgagccgatgacttactggcaggtg | 10 | r = a or g; m = a or c

Any positive result using DNA polymerase nucleic acid as a template that remains questionable for infection (e.g., FRET detection at 38 cycles) was reamplified using TK nucleic acid as a template.

The LightCycler™ master mixture for amplification of the TK nucleic acid sequence contained the following: 0.2 mM concentration of each of the deoxyribonucleoside triphosphates (50 mM KCl, 10 mM TrisCl [pH 8.3]), 4 mM $MgCl_2$, 1.0 µM TK primers, 0.025% bovine serum albumin, 3% dimethyl sulfoxide, 0.2 µM fluorescein-labeled TK probe, 0.2 µM LC-Red 640-labeled TK probe, and 0.03 U of Platinum® Taq (Perkin-Elmer Corp., Branchburg, N.J.) per ml. Each reaction tube received 45 µl of the reaction mixture plus 5 µl of template. A no-template control received 50 µl of the reaction mixture only. Samples underwent 45 cycles of: denaturation at about 95° C. immediately followed by primers annealing to the template nucleic acid for about 15 secs at about 60° C., and elongation of the newly-synthesized strands at about 72° C. for about 12 secs.

Example 6

Sensitivity of Method

HSV was detected in 88 (44%) of 200 specimens. A total of 69 (43%) of 160 genital specimens and 18 (47%) of 38 dermal specimens were positive for HSV DNA. Only two ocular specimens were tested, yielding one positive result. A total of 69 specimens were positive for detection of HSV by both shell vial assay and LightCycler™ PCR. Nineteen additional specimens were identified as HSV positive by the LightCycler™ assay (total number of positive specimens, 88). There were no specimens for which the shell vial assay result was positive and the LightCycler™ result was negative (specificity, 100%). Of the 19 discrepant results (negative by shell vial assay but positive by LightCycler™ assay), all were confirmed as positive for HSV DNA by a LightCycler™ protocol using TK as a template.

Specimens positive by both the shell vial and LightCycler™ assays (n=69) were detected by PCR at an average of 26 cycles (range, 18 to 37 cycles). Discrepant specimens (n=19) were positive after an average of 33 cycles by LightCycler™ assay (range, 24 to 40 cycles). The cumulative rate of detection of the 69 specimens with concordant results reached 100% after 37 PCR cycles, but 81% by cycle 28, whereas the 19 specimens with discrepant results required 40 PCR cycles to achieve positive results for all samples, and only 26% of these samples were detected by cycle 28. Therefore, as expected, specimens positive by both shell vial assay and LightCycler™ PCR apparently have higher copy numbers of HSV DNA than those specimens detected exclusively by the LightCycler™ assay. These results were confirmed experimentally in that the lowest dilution of a suspension of HSV template DNA yielded PCR product in an earlier cycle and in direct proportion to 10-fold less-concentrated dilutions of the viral genome.

Probes designed to detect nucleotide polymorphisms in two base pairs of the 215-bp product of LightCycler™ PCR correctly identified the genotype (HSV-1 or HSV-2) by melting curve analysis in 66 of 69 specimens, whereas monoclonal antibody differentiation of the two serotypes by the shell vial assay was less accurate. Of the 19 specimens with discrepant results analyzed by PCR directed to the TK gene of HSV, 14 were HSV-2 and 5 were HSV-1. The LightCycler™ assay gave concordant genotype results for 18 of 19 (95%) specimens. The melting curves for the four specimens with discrepant results (HSV-1 or HSV-2) overlapped and did not produce distinctive patterns that provided easy visual differentiation of the two genotypes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An article of manufacture, comprising:
a pair of HSV DNA polymerase primers, wherein said pair of HSV DNA polymerase primers comprises a first HSV DNA polymerase primer and a second HSV DNA polymerase primer, wherein said first HSV DNA polymerase primer consists of the sequence 5'-GCT CGA GTG CGA AAA AAC GTT C-3' (SEQ ID NO:1), and wherein said second HSV DNA polymerase primer consists of the sequence 5'-CGG GGC GCT CGG CTA AC-3' (SEQ ID NO:2);
a pair of HSV DNA polymerase probes, wherein said pair of HSV DNA polymerase probes comprise a first HSV DNA polymerase probe and a second HSV DNA polymerase probe, wherein said first HSV DNA polymerase probe consists of the sequence 5'-GCG CAC CAG ATC CAC GCC CTT GAT GAG C-3' (SEQ ID NO:3), and wherein said second HSV DNA polymerase probe consists of the sequence 5'-CTT GCC CCC GCA GAT GAC GCC-3' (SEQ ID NO:4); and a donor fluorescent moiety and a corresponding acceptor moiety.

2. An article of manufacture, comprising:
a pair of HSV DNA polymerase primers, wherein said pair of HSV DNA polymerase primers comprises a first HSV DNA polymerase primer and a second HSV DNA polymerase primer, wherein said first HSV DNA polymerase primer consists of the sequence 5'-GCT CGA GTG CGA AAA AAC GTT C-3' (SEQ ID NO:1), and wherein said second HSV DNA polymerase primer consists of the sequence 5'-CGG GGC GCT CGG CTA AC-3' (SEQ ID NO:2);
a pair of HSV DNA polymerase probes, wherein said pair of HSV DNA polymerase probes comprise a first HSV DNA polymerase probe and a second HSV DNA polymerase probe, wherein said first HSV DNA polymerase probe consists of the sequence 5'-GTA CAT CGG CGT CAT CTG CGG GGG CAA G-3' (SEQ ID NO:5), and wherein said second HSV DNA polymerase probe consists of the sequence 5'-T GCT CAT CAA GGG CGT GGA TCT GGT GC-3' (SEQ ID NO:6); and a donor fluorescent moiety and a corresponding acceptor moiety.

3. The article of manufacture of claim 1 or claim 2, wherein said pair of HSV DNA polymerase probes are labeled with said donor fluorescent moiety and said corresponding acceptor fluorescent moiety.

4. The article of manufacture of claim 1 or claim 2, further comprising a label or package insert having instructions thereon for using said pair of HSV DNA polymerase primers and said pair of HSV DNA polymerase probes to detect the presence or absence of HSV in a biological sample.

5. The article of manufacture of claim 4, further comprising a label or package insert having instructions thereon for using said pair of HSV DNA polymerase probes to distinguish between HSV-1 and HSV-2.

* * * * *

UNITED STATES PATENT AND TRADEMARK OFFICE
CERTIFICATE OF CORRECTION

PATENT NO. : 7,667,025 B2  Page 1 of 1
APPLICATION NO. : 11/140640
DATED : February 23, 2010
INVENTOR(S) : Smith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 130 days.

Signed and Sealed this

Seventh Day of December, 2010

David J. Kappos
*Director of the United States Patent and Trademark Office*

```
                              SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
gctcgagtgc gaaaaaacgt tc                                             22

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide

<400> SEQUENCE: 2
cggggcgctc ggctaac                                                   17

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide

<400> SEQUENCE: 3
gcgcaccaga tccacgccct tgatgagc                                       28

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide

<400> SEQUENCE: 4 cttgccccg cagatgacgc c                                               21

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide

<400> SEQUENCE: 5
gtacatcggc gtcatctgcg ggggcaag                                       28

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide

<400> SEQUENCE: 6
```

```
tgctcatcaa gggcgtggat ctggtgc                                              27

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide

<400> SEQUENCE: 7
cacgctrctg cgggtttata taga                                                 24

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide

<400> SEQUENCE: 8
ttgttatctg ggcgctmgtc att                                                  23

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide

<400> SEQUENCE: 9
cgcgcgacga tatcgtctac gtac                                                 24

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
cgagccgatg acttactggc aggtg                                                25
```